United States Patent [19]

Jahn

[11] Patent Number: 5,275,731
[45] Date of Patent: Jan. 4, 1994

[54] APPARATUS FOR RAPIDLY SEPARATING BLOOD INTO FILTERED FRACTIONS

[76] Inventor: Karl H. Jahn, 42 Kings Grant Rd., Hockessin, Del. 19707

[21] Appl. No.: 723,498

[22] Filed: Jun. 28, 1991

[51] Int. Cl.$^5$ .............................................. B01D 21/26
[52] U.S. Cl. ................................... 210/518; 210/515; 210/516; 422/100; 422/101
[58] Field of Search ........... 210/321.6, 321.67, 321.68, 210/321.84, 360.1, 321.69, 364, 379, 380.1, 382, 514, 515, 516, 518, 450; 494/1, 10, 16, 17, 19, 43; 422/101, 100, 102

[56] References Cited

U.S. PATENT DOCUMENTS

| | | | |
|---|---|---|---|
| 3,488,768 | 1/1970 | Rigopulos | 210/360.1 |
| 4,142,668 | 3/1979 | Lee | 210/514 |
| 4,683,058 | 7/1987 | Lyman et al. | 210/515 |
| 4,853,137 | 8/1989 | Ersson | 210/516 |
| 5,030,341 | 7/1991 | McEwen et al. | 210/515 |
| 5,037,549 | 8/1991 | Ballies | 210/515 |
| 5,039,401 | 8/1991 | Columbus et al. | 210/515 |

Primary Examiner—Robert A. Dawson
Assistant Examiner—Sun Uk Kim
Attorney, Agent, or Firm—Ralph T. Lilore

[57] ABSTRACT

A blood collection and separation system having multi-chamber collection assembly having a longitudinal axis. The assembly in a preferred embodiment is rotatable about its longitudinal axis and an alternate embodiment is rotatable about an axis parallel to its longitudinal axis. A porous separating body at one axial end of one chamber connects with a second chamber and allows flow of the lighter fraction of the blood from the one chamber to the other chamber during centrifugation, but blocks flow of the heavier fraction. Hydrostatic forces are created during centrifugation to cause flow of the lighter fraction through the body into the other chamber. Preferably the surface of the separating body which faces the first chamber slopes away the spinning axis so that centrifugal force tends to dislodge any particles of the heavier fraction which might be lodged on the surface. The assembly of the present invention affords handling of blood for testing or analysis without human exposure to the blood components.

10 Claims, 6 Drawing Sheets

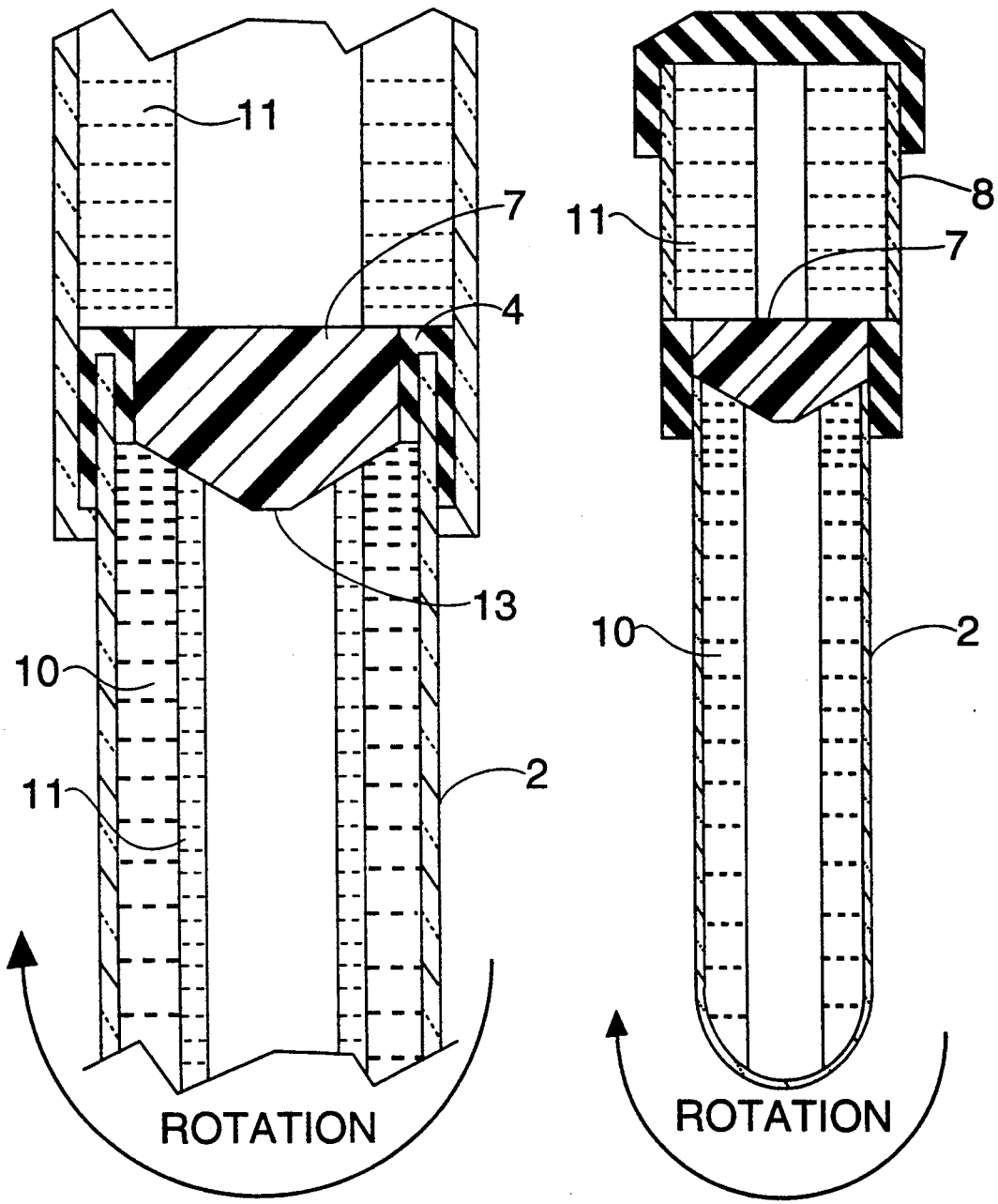

APPARATUS FOR RAPIDLY SEPARATING BLOOD INTO FILTERED FRACTIONS

FIELD OF THE INVENTION

This invention relates to a method and an apparatus for rapidly separating blood into red blood cells and filtered serum or plasma, and performing examination therewith, and has particular application to separation using a centrifuge and a separating device.

DESCRIPTION OF THE PRIOR ART

Much of modern analytical medicine relies upon the examination of blood and blood components. Blood is commonly drawn by syringe, or into an evacuated tube as in FIG. 1, such as a Becton Dickenson Vacutainer ® tube. Many specimens are drawn remotely or in physicians offices and are then transported to a central analysis site, such as a reference laboratory. Others are essentially processed and examined on site in clinics or hospitals. In all cases, it is desirable to minimize human contact with the sample in order to reduce the risk of infectious disease transmittal. The sensitivity of modern analysis equipment also makes it imperative that only totally inert materials contact the blood, and that misdiagnosis through cross contamination between samples is totally eliminated. Commonly used thixotropic gels, as well as fibrin strands in blood components can act to compromise the reliability and accuracy of these automated analyzers. Further, samples must be prepared for analysis as rapidly as possible, particularly in cases of medical emergency (or stat processing).

Separation of the blood into phases is usually a necessary part of the analytical procedure. One method of examining blood samples involves coagulating of the blood sample and subsequently separating the sample by conventional centrifugation into components consisting primarily of heavier phase red blood cells and a lighter phase liquid called serum. A second method prevents coagulation through the addition of anticoagulants to the blood. The blood is then usually separated by centrifugation into the heavier red blood cell components and lighter blood plasma. It is generally considered important to recover as much of the available serum/plasma component as possible for analysis. This is particularly the case with pediatric or geriatric patient samples, where frequently only a small amount of patient sample can be obtained. In all cases, it is critical to the desired examinations that red blood cells are totally separated and are not present in either the serum or plasma. It is also desirable that the specimen be analyzed as soon as is practical after the separation has occurred.

Conventionally, the process of separation is accomplished in a centrifuge which spins the entire sample, contained in a tube, around an axis of rotation for approximately 10 to 15 minutes and subjects it to a centripetal acceleration of approximately 1200 times gravity. These devices require counterbalanced loading, and frequently generate considerable amounts of energy since the sample must be cradled in a rotor of significant mass which is subject to the same gravitational force as the sample. These devices occasionally fail, potentially exposing the user to hazardous aerosols generated by the sample. The significant amount of spin time required by these devices furthermore generates frictional heating of the rotor chamber, which must be overcome either by an expensive refrigeration system, or by air cooling of the chamber, which again potentially exposes the user to said hazardous aerosols, particularly in the event of a rotor failure or tube breakage.

Once the serum or plasma has been separated, great care must be taken to avoid the reintroduction of red blood cells, since this could invalidate the examination process. In those cases where blood components are analyzed remotely, as with a reference laboratory service, a permanent barrier must be established between the separated phases. To address this difficulty, a number of methodologies have been devised. On method consists of carefully pouring the serum or plasma from the primary collection tube into a secondary transport tube. This method exposes the clinician to potentially hazardous aerosols of the serum or plasma, does not yield all of the available serum or plasma, and risks re-mixing during the handling and pouring process. A second method relies on the movement of a material with density specifically between that of serum and the heavier cell components. This viscous thixotropic gel is specifically configured as part of a blood collection tube system. During centrifugation of this gel in a blood filled-tube, it migrates to a position between the serum (or plasma) and red blood cells (See U.S. Pat. Nos. 3,647,070; 3,852,194; 3,986,962; 4,012,325; 4,055,501; 4,083,784; 4,189,382; and 4,350,593). Since the gels, however, perform no significant wiping or filtering action on the sample, fibrin and residual cells (which can cling to the tube wall during centrifugation) may remain in the serum (or plasma) layer. Furthermore, particles of the gel itself can remain in the sample. Modern automated analysis equipment can be caused to malfunction through the presence of fibrin or gel particles. These gel particles, and in particular the presence of red blood cells can furthermore lead to incorrect or misleading test results. In the interest of convenience, and because of the need to achieve relatively effective barriers between red blood cells and serum or plasma, in spite of their shortcomings, gel based serum separation tubes now account for approximately 25% of the total blood collection market.

A further centrifugally activated serum separating concept consists of a piston having a specific gravity between serum and red blood cells which is fitted into a centrifuge tube. Such devices, some of which include combinations of pistons and gels and/or filters, are described by U.S. Pat. Nos. 3,909,419; 3,919,085; 3,920,557; 3,926,646; 3,931,018; 3,951,801; 3,957,654; 4,001,122; 4,088,582; 4,152,270; 4,14,690; 4,202,769; 4,417,981; 4,425,235; 4,443,345; and 4,492,632. These devices are all designed to function in standard centrifuges, and in order to effectively perform their wiping action require tight tolerances between piston and tube, resulting in relatively high costs. Indeed, these devices have found only very modest market acceptance.

Other methods, such as described by U.S. Pat. No. 4,021,352 attempt to use a filter medium to directly achieve the separation of blood into its components. The medium described, however, is unable to maintain a separation barrier over time since the channel size described permits the passage of red blood cells, and the process described in both cumbersome and technique-dependant. U.S. Pat. No. 4,639,316 describes a device utilizing vacuum pressure preapplied in manufacturing of the blood drawing tube to directly filter and separate red blood cells from plasma as part of the blood drawing procedure. While the device does not require centrifugation, it cannot be used to examine blood serum, and has the practical limitation of requiring the blood drawing tube to be attached to the patients vein for approximately 30 seconds. Access to the filtered plasma would also require greater care than currently necessary in order to avoid dripping plasma as the filtering element is removed from the processing tube. U.S. Pat. No. 4,946,603 also does not require centrifugation, but is described as practical only for separating 0.5 ml of blood, too small an amount to be useful for the broad range of examinations usually performed.

U.S. Pat. No. 4,492,634 describes still another method of filtration which again relies on conventional centrifugation, but has the added expense of a double-stoppered tube, and makes no provision for filter clearing.

A number of concepts have also been described which aim to achieve filtered serum or plasma from separated blood. U.S. Pat. No. 4,369,117 combines the previously described idea of a piston with a filtering element. This device also functions only in a conventional centrifuge, and is useful only for serum separation. In order to minimize clogging problems common with filtering devices used to separate blood components, it has a filter pore size greater than that of red blood cells. This, however, also allows red blood cells to mix with serum, therefore substantially reducing its utility. U.S. Pat. No. 4,522,713 describes a similar but more complex device, which also requires conventional centrifugation, and has not found widespread market acceptance. Among its practical limitations are the requirement of separating, by centrifugation, the blood into fractional components prior to filtration. At that point, the device must be introduced to the centrifuge tube, respun, and with the further constraint of a practical limitation of recovering only 50% or less of the available fluid (and that only with flat bottom tubes, which are not conventionally in use).

Still other filtration devices such as described by U.S. Pat. Nos. 4,464,254, and 4,602,995 require separated blood fractions prepared and layered by conventional centrifugation and are usually not designed to act as permanent barriers between the fractions or to recover all available blood serum. An exception is described in U.S. Pat. No. 4,957,637, which does claim to create a permanent barrier, but still requires conventional centrifugation prior to a separate filtering step.

U.S. Pat. Nos. 4,828,716 and 4,846,974 describe a system wherein the blood collection chamber is rotated about its own axis to effect the separation of blood into its components. Such axial separation can reduce the processing time to less than 1 minute as compared to the aforementioned 10 to 15 minutes required by conventional centrifugation. The difficulty with this process, however, is the method of achieving phase separation once the system comes to rest. In one case, the sample must first be transferred from the collection tube into a special, and relatively expensive secondary processing cassette, where a gel substance is used to create the separation barrier. In the other, a probe is inserted directly into the sample chamber, and an elaborate sensing system is employed to determine when the separation process has been completed. The probe, of course, is a potential source of sample contamination and cross-contamination between samples. This has been anticipated by the authors, and a further embodiment claims to address this concern with an elaborate construction of dual tubes, one way valves, filters, and a syringe like action. Both embodiments, however, rely on mechanically changing the chamber volume, thereby expressing one of the phases into a secondary chamber component, and sensing when the separation interface has been reached in order to terminate the process. This procedure is inherently unreliable, requires expensive hardware, as well as a new, unique, and also expensive blood collection tube.

Beyond the mechanical elements of blood processing and their inherent shortcomings, the current methodologies are also largely labor-intensive, and fraught with high potential for error. Modern analyzers have the capability to process a very broad range of clinical data on a single patient sample in a matter of a few minutes. Current practice, however, is to draw substantially more patient sample than is required by these analyzers. The samples are then divided into a number of separate aliqots, each of which must be separately labelled, often by hand, as well as manually transferred into separate and open containers by pipetting. This labelling step can lead to human error, resulting in misdiagnosis, while the aliquotting step exposes a laboratory technician to the hazard of infection from the patient sample. Furthermore, these steps add additional processing time and cost.

There are currently methodologies which propose to utilize the originally drawn patient sample tube directly by the analyzer after centrifugation. This method, however, still requires drawing substantially more patient sample than required for analysis. Furthermore, a method of stopper removal or stopper piercing is required in order to access the serum or plasma. Once accessed, there is the further complication of avoiding the red cell, or gel interface, and subsequent disposal or washing of the piercing needle. Finally, a method to avoid spillage or the formation of aerosols within the analyzers must be developed.

SUMMARY OF THE INVENTION

The invention embodies a separator that can be mounted on a standard blood collection tube or syringe, or configured integrally with such a device, in order to rapidly achieve filtered and permanently separated blood components under the influence of centrifugal acceleration, preferably axially-oriented.

In one embodiment, the stopper is first removed from a standard, blood filled collection device, and the separator installed in its place. This can be accomplished manually, or automatically by machine in those instances when it is desirable to eliminate human exposure to the blood sample. The tube and separator assembly is then simply inserted into a centrifuge which spins the entire assembly about its own axis, or a remote or offset axis substantially parallel to the tube axis, for approximately one minute. Radial forces within the system separate the heavier red blood cells and move them to the outer tube wall, leaving the lighter serum or plasma near the tube's center. These same radial forces also set up axially oriented hydrostatic pressure forces which push fluid against the separator.

The separator is a body of a porous material, such as a filter, a membrane or a flow restricter, which exhibits a pore size or opening sufficient to permit passage of particles of the desired lighter phases, yet restricting passage of the heavier red cell components, as well as fibrin and other undesired blood components. The shape of the separator can be configured so that it has an inclined surface exposed to the collection chamber. The more powerful radial forces act to remove red blood cells and fibrin from its inclined surface, thereby clearing a path for the hydrostatically driven lighter phases to pass through into a secondary collection chamber. By utilizing a hydrophobic material, or an appropriately channeled geometry within the separator, fluid will only pass through the separator under pressure, such as hydrostatic or centrifugally generated, and a permanent barrier between the separated and filtered phases can be achieved.

Advantageously, this concept eliminates the need for probes, valves, sensors or gels, which can compromise sample integrity and add complexity and cost. It is thereby also capable of recovering all available serum or plasma. The separator is further capable of acting as a transport tube, as well as a self contained dispensing device. The present invention can therefore fully accommodate the advantages of today's sophisticated modern analyzers by rapid centrifugation (integral to the analyzer if desired), by eliminating the need for aliquotting, relabeling, and additional handling, and by capturing all available patient serum or plasma and presenting it to the analyzer in filtered, pre-measured and easily accessible form. This fully integrated system thereby totally automates the processing of blood, significantly speeding up the process, while eliminating the potential for sample labelling error as well as infection of the processing staff.

BRIEF DESCRIPTION OF THE DRAWINGS

FIG. 5 is an enlarged fragmentary sectional view of the assembly of FIG. 3 spinning on its axis.

FIG. 6 shows the assembly of FIG. 3 during the separation process.

DETAILED DESCRIPTION

Figure 1:
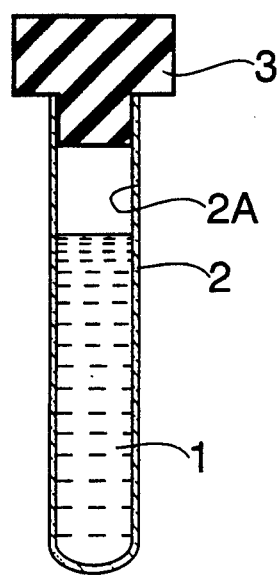
FIG. 1 is a sectional view of a filled standard evacuated blood collection tube.
Figure 2:
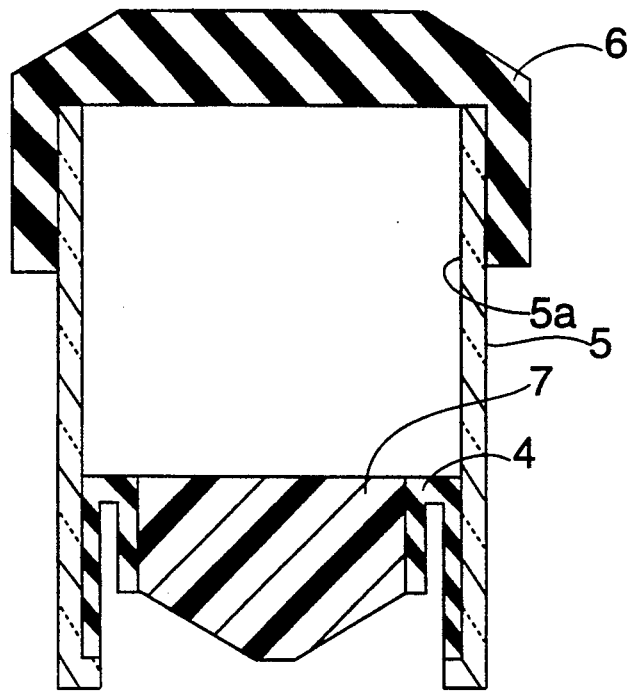
FIG. 2 is an enlarged sectional view of the preferred embodiment of separating body mounted in an attachment of the present invention.

The present invention relates to a separating device that can be assembled with a collection container for use in a centrifuge. When assembled, the device provides a pair of chambers within the assembly. Whole blood is collected in the first chamber and during the centrifuging, one fraction of the blood, for example the serum or plasma passes through the separating device into the other chamber. When whole blood has been drawn into the blood collection chamber, it can either be allowed to clot naturally by waiting approximately 30 minutes, it can be induced to clot more rapidly through the addition of clot activators, or it can be prevented from clotting through the addition of clot inhibitors. Clotted blood yields serum, and unclotted blood yields plasma after separation.

In the embodiment of the invention illustrated in FIGS. 1 through 8, a separating body 7 is mounted in one end of an attachment 8 adapted to fit on the open end of a standard collection tube after removal of the stopper closure 3. After removing the stopper 3, one end of the attachment 8 may be inserted in its place to form an assembly of the tube 2 and the attachment 8.

At its one end, the attachment 8 has a seal 4 into which the open end of the tube 2 fits to assure that the blood will not leak from the tube during processing. Above the seal 4 the attachment has an outer wall 5 forming a collection chamber 5a which is closed by a cap 6 fitted on the opposite end of the wall 5. Centrally of the seal 4, a porous partition body 7 is provided to serve as a separation device between the chamber 5a above the seal and the interior chamber 2a of the collection tube. The separator 7 is operable to selectively pass fluid fractions with particles below a given threshold size. When assembled as shown in FIG. 3, the assembly provides a sealed container for the blood 1 collected in the tube 2.

It should be noted that in most blood laboratories, the collection tubes 2 are of standard diameter and thickness so that the attachments 8 for the tubes may be interchangeably used with the collection tubes, and adoption of the present invention will not require modification of the existing blood collection techniques, avoiding the necessity for substantial replacement of supplies as is required by the prior art systems described above.

Figure 3:
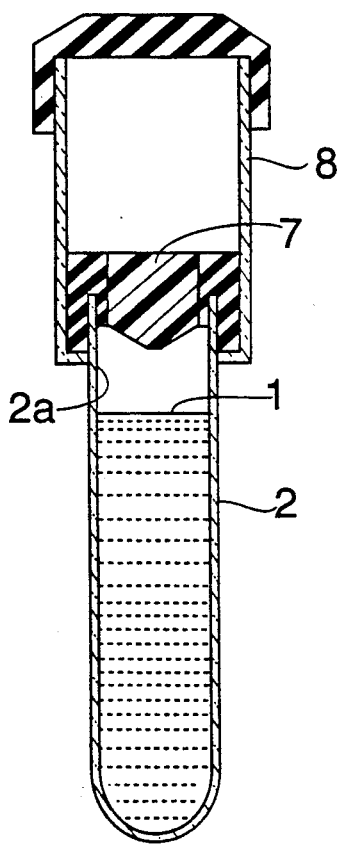
FIG. 3 is a sectional view of an assembly of the attachment of FIG. 2 mounted on a standard blood collection tube with stopper removed.
Figure 4:
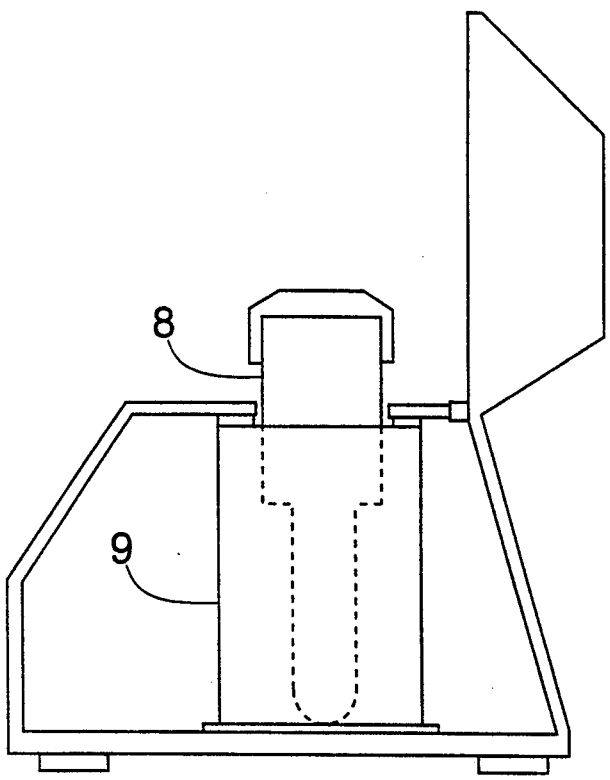
FIG. 4 is a diagrammatic view of the assembly of FIG. 3 contained in an axial centrifuge.

In the preferred embodiment of the invention, the assembly shown in FIG. 3, consisting of the collection tube 2 and the attachment 8, is inserted into a specially constructed centrifuge as shown diagrammatically in FIG. 4. The centrifuge has a drive motor 9 with a central rotor adapted to accommodate the assembly of the collection tube 2 and the attachment 8. Energization of the motor 9 rotates the assembly and spins the assembly about its axis to effect centrifugal separation of the various fractions of the blood sample 1 within the center of the tube 2. The speed of separation of the fractions is a function of the rotational speed of the rotor. The assembly of the attachment 8 and the tube 2 is symmetric about its longitudinal axis, and does not require balancing as do tubes spun in conventional centrifuges.

As shown in FIG. 5, as the rotor and the assembly are accelerated, the heavier blood components 10 are forced to the outside wall of the blood collection tube 2 and the lighter plasma or serum 11 is displaced towards the center of the tube. The threshold porosity of the separating body 7 is selected to pass the cells of the lighter fraction but to block passage of the heavier cells so that the lighter fraction 11 is free to pass through the separation device 7 and into the chamber 5a defined by the outer wall 5 of the attachment 8. The radius of the standard collection tube is on the order of 5 mm as compared to a length of approximately 70 mm, radial separation of the fractions of the blood samples requires a short path length as opposed to the long path length provided when the separation is axially of the chamber. Due to the high acceleration and short path length, separation is effected in one minute or less. This rapid separation process makes the invention ideal for situations when tests must be performed very rapidly, such as in stat or emergency situations.

It should be noted that the wall 5 may be offset outwardly from the wall 2, so as to insure that the wall is greater in diameter than the inside diameter of the sample in the chamber 2a, so that the centrifugal force on the blood sample generates a hydrostatic pressure differential between the chambers 2a and 5a, which can act to drive the serum fraction 11 through the porous separating body 7 from the chamber 2a into the chamber 5a. This is illustrated in FIG. 5.

As shown in FIG. 5, the porous body 7 has a downwardly facing surface facing the chamber 2a in the collection tube. The surface extends across the full width of the tube and merges into the seal 4 at the outer wall of the collection tube. As shown, the surface 13 is substantially conical and starts at the wall of the collection chamber and is inclined relative to the radial direction toward the central axis of the collection chamber 2a. The inclination of the surface 13, when spun in the centrifuge about its axis, throws outwardly any particles of the heavier fraction 10 which are above the threshold size of the body 7 and may lodge on the surface 13 as the lighter fraction 11 flows through the pores into the chamber 5a. This self-clearing feature eliminates the clogging problems associated with previous attempts to effect simultaneous filtration and separation. Also, since the lighter phases are drawn out of the original collection tube, the need for wiping red cells, which potentially can create cell damage, from the tube walls, as described in prior patents and publications, is entirely eliminated.

FIG. 6 shows how the assembly of the attachment 8 and the tube 2 after separation has been completed and just prior to deceleration and stopping of the centrifuge. Sensing of the separated phases is not necessary, since only light phases such as plasma or serum can pass through the separation device. Previously described inventions that rely upon sensing of the blood phase interfaces critically require specific placement of all labels to assure that the sensing window was not obscured by the label. This device, on the other hand, may accept labels that completely cover the tube, or that are in any manner randomly applied. Also, since these lighter phases are passed through the separation device interiorly through hydrostatic pressure, the need for mechanical force or vacuum as described by previous inventions is eliminated. This overcomes problems of hemolysis, which can occur if delicate blood components are forced to separate through mechanical pressure. Also, in systems where there is a need to mechanically change the separation chamber volume, it is often difficult to recover more than 80% of the available serum or plasma volume. This is particularly true when only a small amount of blood is available, as is frequently the case with pediatric or geriatric patient samples. The curved portion of the collection tube base, or the shape constraints of the various separator schemes described in previous patents and publications, makes these systems notoriously inefficient, as does the need of sensing the phase interface between the blood phases. This invention, however, is capable of recovering substantially all available serum or plasma.

Figure 8:
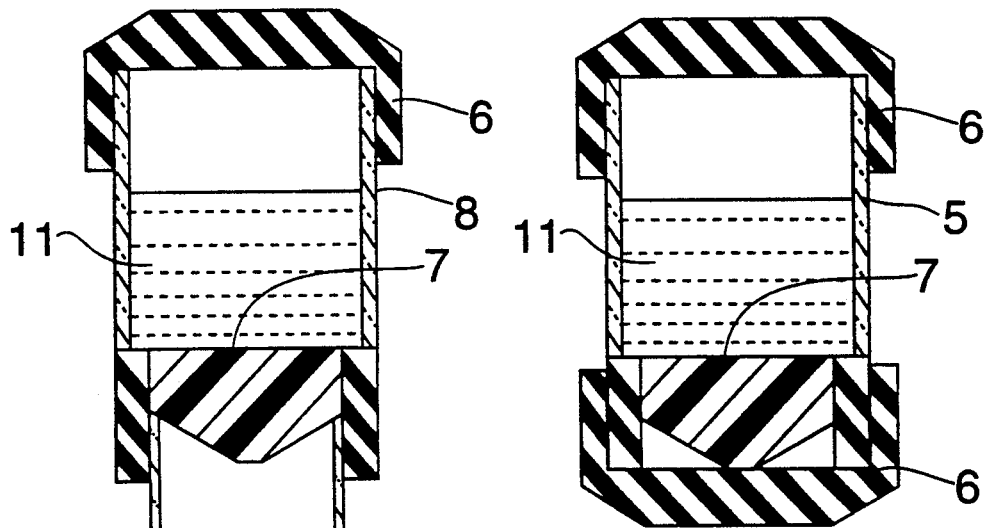
FIG. 8 shows the attachment with caps to serve as a serum or plasma transport tube.
Figure 7:
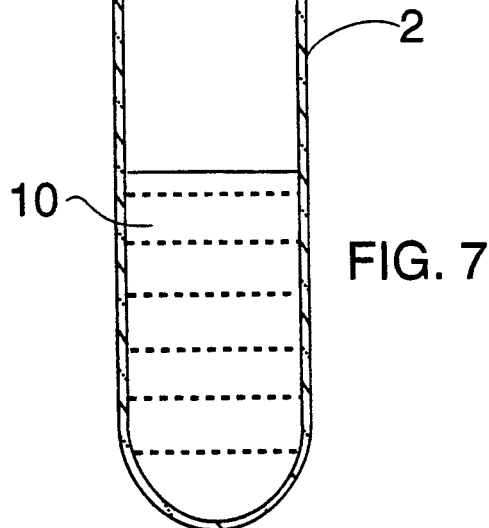
FIG. 7 shows the assembly at rest after completion of the separation process.

FIG. 7 illustrates the position of the fractions upon stopping of the centrifugal spinning of the assembly. The separated fluids come to rest as shown in FIG. 7. By utilizing a hydrophobic material as part of the porous body 7, or by appropriately configuring the geometry of the device, i.e. through the inclusion of a serpentine fluid trap, plasma or serum 11 will not flow back into the original blood collection chamber 2a, thereby effecting a permanent separation without the need for valves or gels as described in previous patents and publications. The entire assembly, including the blood collection tube 2, may now be shipped to a reference lab for processing. Alternatively, the cap 6 may be removed to afford removal of all or part of the serum or plasma as aliquots. If desired the serum or plasma collection attachment 8 may also be removed from the collection tube and the end of the attachment with the separation body 7 may be covered with a second cap 6 as shown in FIG. 8. This allows direct access to the heavier blood components still left in the original blood collecting tube and overcomes the deficiencies of other previous inventions. The resulting serum or plasma transporting assembly of FIG. 8 is lighter than blood collection tubes with gels or other internal barriers thereby reducing shipping and handling costs. The transport assembly illustrated in FIG. 8 can also be configured to resemble a sample cup that would make it suitable for direct insertion into an automated analyzer, thereby eliminating the need for secondary aliquoting and potential human exposure, or error, due to mislabeling or handling. Through-the-cover sampling by the analyzer may also be readily accomplished in such a system. By utilizing an automated device to remove the serum or plasma collection attachment 8 from the blood collection 2, the need for human exposure to blood components is also eliminated.

Figure 9:
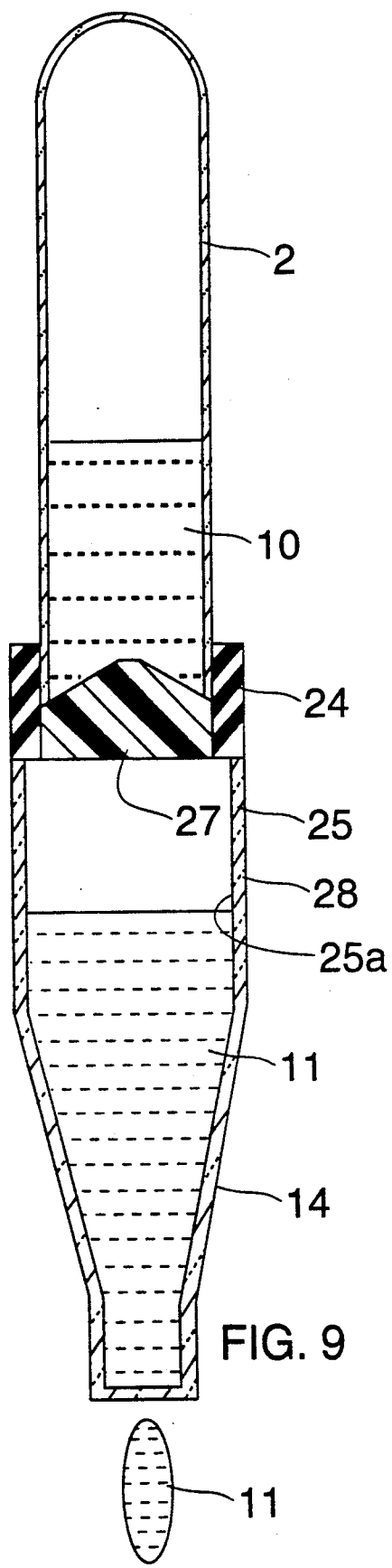
FIG. 9 shows a second embodiment of an attachment with a separating body assembled with an inverted standard blood collection tube, which attachment acts as a pipette dispenser after separation has been completed.
Figure 10:
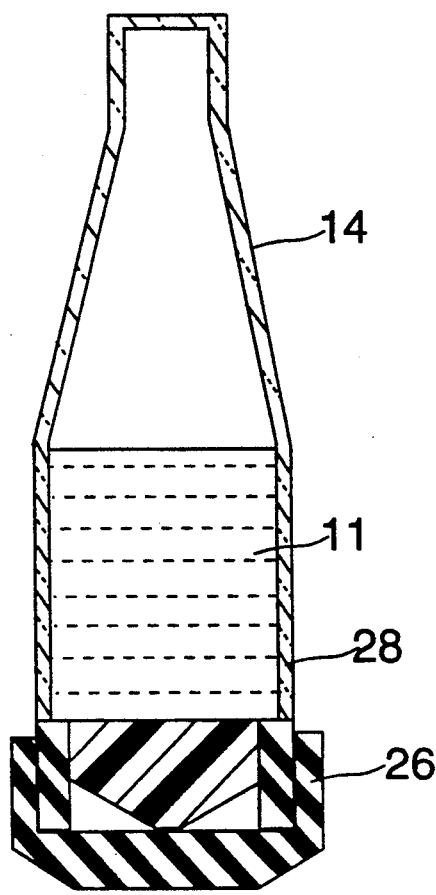
FIG. 10 shows the second embodiment of the attachment with a cap for use as a serum or plasma transport tube with pipette dispenser.

A second embodiment of the invention is illustrated in FIG. 9 in which a pipette tip is provided at the opposite end of the chamber of the separation attachment in place of the cap 6 described in the first embodiment. In other respects, the attachment is similar to the first embodiment. In this embodiment, the attachment is designated 28 and has an outer wall 25 defining a collection chamber 25a. At one end, the attachment has a seal 24 with a central separation body 27 adapted to interfit with the open end of a standard collection tube 2. At the opposite end, the cylindrical wall 25 of the attachment 28 tapers to form a pipette tip 14 which, when inverted as shown in FIG. 9, affords dispensing precisely desired volumes of serum or plasma, once separation has been completed, avoiding the need for additional transfer or aliquoting steps. The attachment 28 may be used as a transport tube as shown in FIG. 10 by providing a cap 26 for the sealing end of the attachment.

Figure 11:
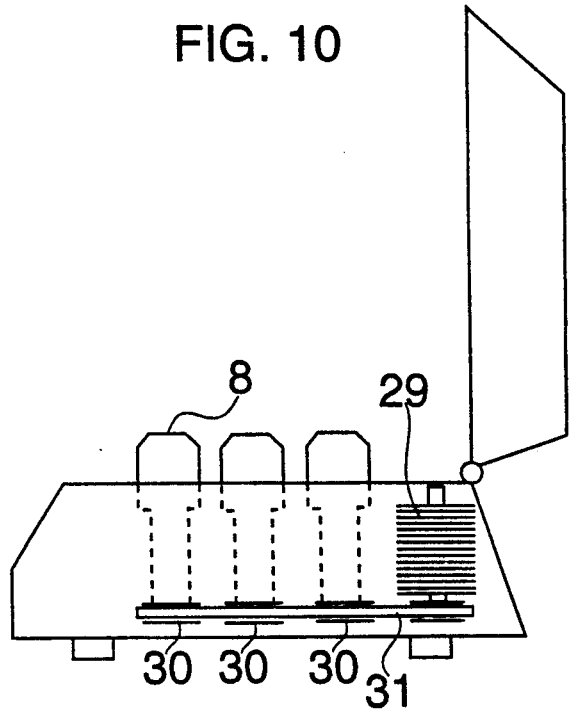
FIG. 11 is a diagrammatic view of an axial centrifuge capable of processing multiple assemblies.

Since the devices described herein are extremely simple in construction, and do not require complex sensing or mechanical controls, they are also inherently very reliable, rugged and cost-effective to produce. In particular, this method of processing lends itself to the cost-effective construction of an automated centrifuge that can spin multiple tubes simultaneously, as shown diagrammatically in FIG. 11. Whereas conventional centrifuges normally found in the clinical laboratory can batch-process about 60 tubes per each 15-minute run, yielding a throughput of about 240 tubes per hour, a multiple tube device as shown in FIG. 11, even if configured to spin only 10 tubes per one-minute run, could process 400 tubes even if a generous 30-second loading and unloading period is allowed. This centrifuge would be much smaller than a comparable conventional centrifuge with corresponding throughput, and since balancing is not required, and since tube loading location is always constant, the multiple tube device of the present invention would be ideally developed into a totally automated centrifugation system. Such a system could include loading and unloading of tubes, bar code label identification, as well as sensing of sample quality in the collection chamber while the device is spinning. Referring to FIG. 11, the centrifuge has a drive motor 29 which is coupled to a plurality of rotors 30 by a common drive mechanism, such as a belt 31. Each rotor is adapted to mount an assembly of a collection tube 2 with an attachment 8 and the single drive motor 29 may be coupled to ten rotors without undue loading of the motor or the drive mechanism.

Figure 12:
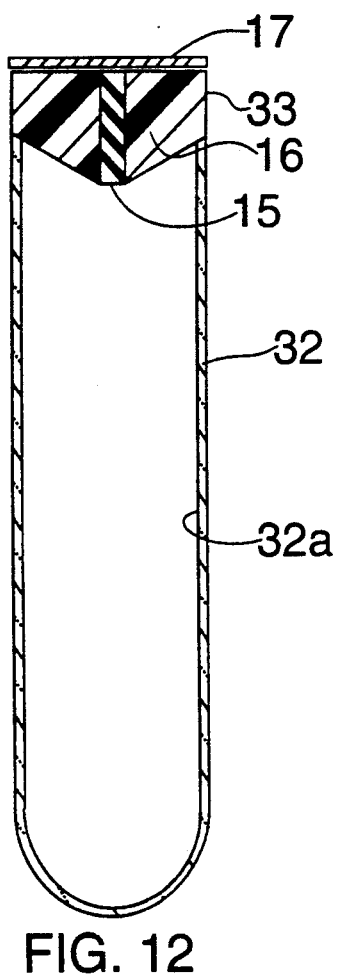
FIG. 12 is a sectional view of a blood collection tube with a separating body made integral with the tube.
Figure 13:
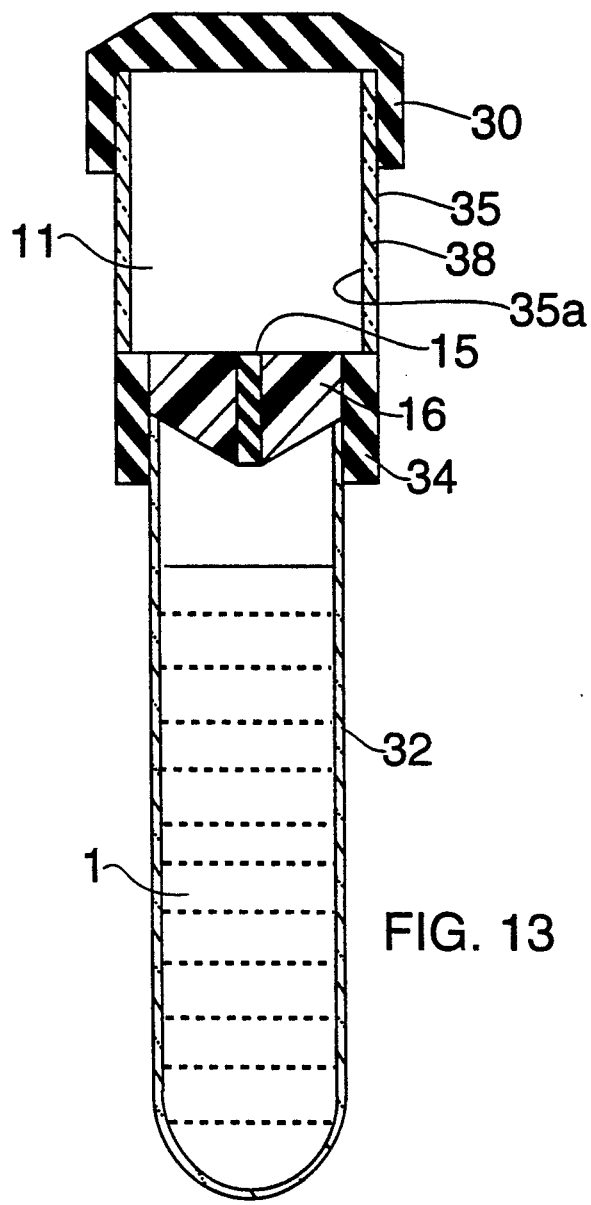
FIG. 13 shows a third embodiment of an attachment assembled with a separate blood collection tube having an integral separating body as in FIG. 12, with a cap installed to serve as a collection vessel.

The invention may also be practiced with a prepackaged blood collection syringe or collection tube 32, such as shown in FIG. 12. In this embodiment of the invention, the collection tube 32 provides a collection chamber 32a which is closed at the top by a stopper 33 which is sealed in the open end of the tube 32. The stopper is in three parts, consisting of a self-sealing core 15, that can be pierced by the collection needle in a similar way to current blood collection tube stoppers. Surrounding the core at 15 is a porous separation body 16 similar to the separation body 7 of the previously-described embodiment. The stopper is covered with a foil seal 17 which acts as a vacuum-retention barrier. To draw blood, the foil 17 is pierced, as is the self-sealing core 15. In order to process the sample as described in the previous embodiments of this invention, the foil is peeled away, and a serum or plasma collection attachment 38 is mounted on the tube 32 as shown in FIG. 13. The attachment 38 has a cylindrical wall 35 defining a collection chamber 35a. At one end, the wall is capped by a cap 36 and at the other end, an internal seal is provided at 34 to seal with the upper end of the collection tube 32. With the attachment 38 in place, the assembly is now ready for processing, significantly without the need for removal of the stopper or other closure and within a closed system.

Since the volume of the serum or plasma collected in the collection chamber 35a can be limited by the volume of the chamber, it is now also possible to create precisely-measured quantities of plasma or serum for presentation to the analyzer, or for interaction with pre-measured test reagents for specific diagnostic tests. Other embodiments of the invention can therefore also include a device to automatically aliquot specifically predetermined test volumes from the spinning assembly into analyzer-ready sample cups.

Figure 14:
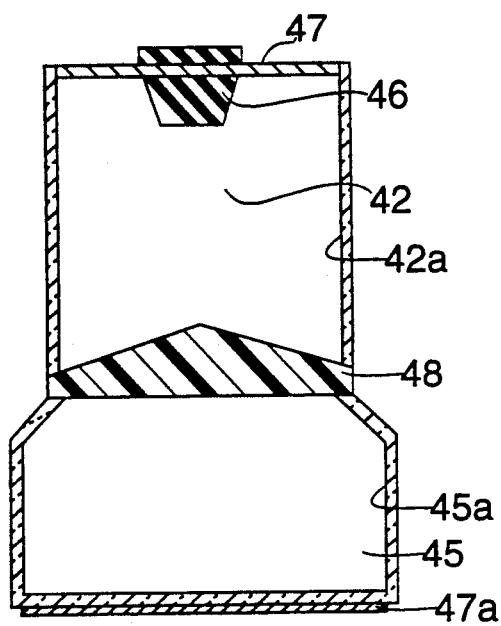
FIG. 14 shows another embodiment of the invention embodying a separation body within a self-contained assembly, forming a closed system.
Figure 15:
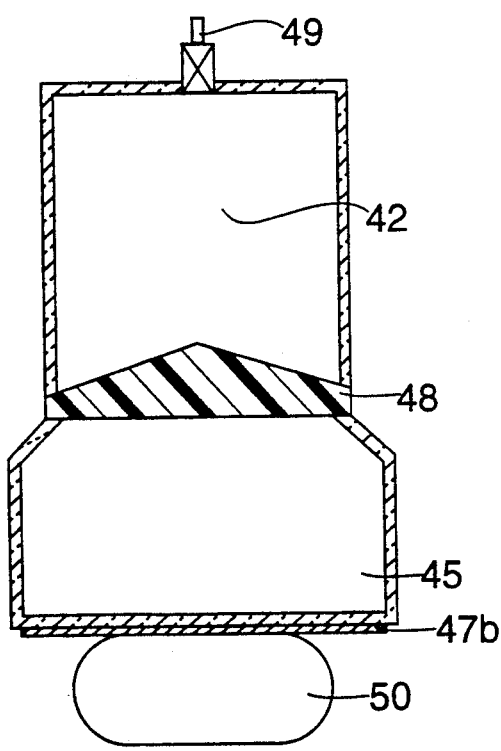
FIG. 15 shows another system with a separating body as used in FIG. 14, that eliminates the need for pre-evacuation.

FIG. 14 illustrates a further embodiment of the invention wherein an assembly acts as a self-contained closed system, which could fully automate the blood processing process. In this embodiment, the blood is collected in the upper part 42 of the assembly which provides a collection chamber 42a. The top wall of the upper part of the collection chamber 42a has a central self-sealing core 46 which is part of a foil overwrap closure 47. The lower end of the chamber 42 is defined by a separation body 48 similar to the separators 7 described above. The porous separator body 48 is disposed between the upper part 42 and the lower part 45 which defines a lower chamber 45a. The lower end of the chamber 45 is closed by an easily pierceable membrane or foil 47a. Blood is introduced into the collection chamber 42a through the core 46 and the assembly may be spun to separate the plasma or serum or other light fractions through the porous body 48 into the lower collection chamber 45a. The serum and plasma may be withdrawn by piercing the closure 47a and the heavier fractions may be withdrawn by piercing the closure 47.

This device can also be configured to be an analyzer, drawing only as much patient blood as needed for analyzer processing. With this reduced volume need, it is possible to also eliminate the need for a pre-evacuated collection tube, and blood collection into the blood collection chamber 42a may be achieved by replacing the core 46 with an inlet port 49. A suction device 50 is mounted at the lower end of the collection chamber 45 by a closure element 47b. The suction device 50 may be a simple suction bulb to evacuate or reevacuate the chamber 42a and/or generate a negative pressure within the chambers 45a and 42a. Since the whole blood does not flow through the separation device 48, the lower closure 47b with the suction device attached may be removed and replaced with the lower closure 47a as described above before centrifuging. With the closure 47a in place, the assembly may then be inserted in the centrifuge and operated as described above in connection with FIG. 14.

Figure 16:
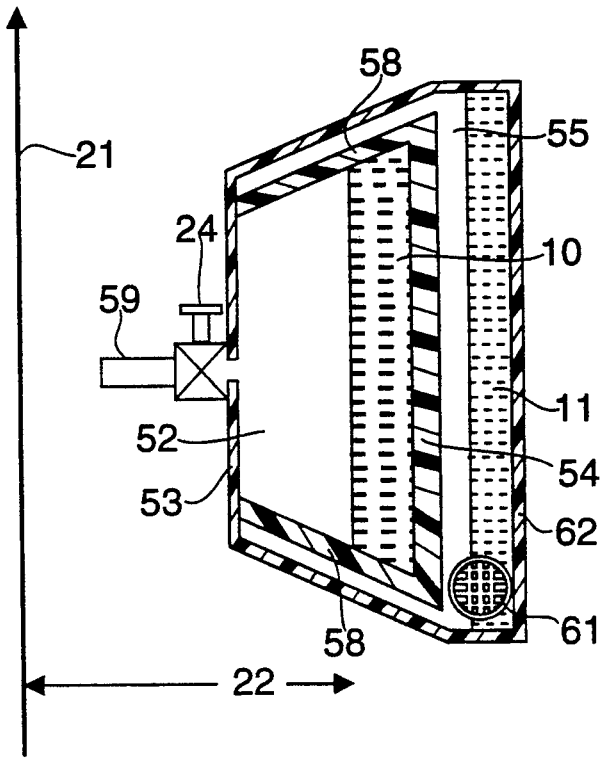
FIG. 16 shows a blood collection system employing an assembly of a collection tube, a collection chamber, and a separating body that can be centrifuged about an axis of rotation which is offset from and parallel to the axis of the assembly.

A further embodiment of the invention places the collection assembly offset from the axis of rotation as shown in FIG. 16. This system has the advantage of requiring substantially lower rotational speed than the above systems which spin the collection assembly about its own axis. The reduction in rotational speed results from the fact that the centrifugal force on the red cell-splasma interface is directly proportional to the distance 22 of the interface from the axis of rotation 21. The greater this distance 22, the lower the speed requirement for separation. The lower speed system of this embodiment can have the effect of reducing processing noise and component costs, and can speed up processing time. In this embodiment, the geometry or shape of the collection assembly may also be designed to take full advantage of the centrifugal and hydrostatic pressures created within the system.

In the illustrated example, the collection assembly consists of two separable and adjacent chambers whose geometry is essentially flat rather than cylindrical as in most conventional blood collection devices. The system has a blood collection chamber 52 having an inner wall 53 adjacent the axis of rotation 21 and an outer wall 54 spaced outwardly from the inner wall 53. Separator bodies 58 are provided between the walls 53 and 54 to form the side walls of the chamber 52. The inner wall 53 has an inlet port 59 for accessing the collection chamber 52. A plasma collection chamber 55 is positioned outwardly of the chamber 52 and extends inwardly to surround the side walls of the chamber 52 in the area of the separator bodies 58. The chamber 55 has an access port 61 adjacent its outer wall 62. In operation, the whole blood is drawn into the collection chamber 52 and upon centrifuging of the assembly, the heavier fraction is displaced towards the outer wall 54 and the lighter plasma or serum fraction is displaced inwardly and flows through the separation bodies 58 into the outer chamber 55 by reason of hydrostatic forces and is displaced toward the outer wall 62. As shown in FIG. 16, the heavier fraction 10 remains in the chamber 52 whereas the lighter fraction 11 is displaced into the outer chamber 55.

A novel method of blood collection with this assembly may be achieved by evacuating the inside of the chambers prior to blood collection. The inlet port 59 has a valve 24 which may be operated to connect the inlet port 59 with the evacuated chambers 52 and 55. By placing the inlet port 59 in direct proximity to blood resulting from a skin prick, and subsequently opening the valve 24, blood is sucked into the chamber 52 for processing. This system is advantageous in designing collection devices specific to individual tests or analyses. This configuration of the collection assembly enables the outer walls 54 and 62 of the collection chambers 52 and 55 respectively to be manufactured as flat plates or collection dishes and visual analysis of the separated components will be enhanced by elimination of the curvature created by cylindrical tubes and chambers to facilitate examination. The assembly provides independent access to individual sample aliquots.

In order to facilitate the process of separation, it is also possible to add external vacuum forces to the chamber 55, thereby assisting the naturally created hydrostatic forces within the system. The port 61 in the chamber 55 may also be used to effect evacuation of the serum or plasma from the chamber into a separate vessel, thereby further eliminating the possibility of backflow of serum or plasma into the blood collection chamber 52.

A further embodiment would integrate the assembly directly into an automated analyzer. This would permit the analyzer to accept whole blood in a closed system and effect all sample separation and analysis steps without human exposure to the blood sample under analysis. The invention described herein is not limited to the separation of blood but can advantageously be used in the separation of any multiple phase liquid or other fluid where separation may be enhanced through the benefits described herein. Effectiveness can further be enhanced or customized by choice of separation material utilized in the separation bodies. Multiple filters or membranes may be layered in the separation body to achieve specific goals as dictated by the end use, and multiple second chambers may be provided to separate the plasma into individual sample aliquots.

Further modifications and enhancements of the invention will occur to those skilled in the art and are intended to be embraced within the invention as defined by the attached claims.

I claim:

1. A device for collection of fluid resulting from centrifugal separation of a particulate fluid sample having fluid fractions with particles of respectively different particle sizes, said device being attachable to a substantially cylindrical blood collection tube having a vertical axis and an open or openable end on said vertical axis, said attachment being a said open or operable end thereof, said collection tube being a container for said sample and constituting a first chamber when said device is attached thereto, wherein said device comprises an attachment having two ends one of which having attached thereto a separation body operable to selectively pass fluid fractions with particles below a threshold size, said separation body being releasably and sealingly engageable with said open or openable and of said collection tube, and defining when attached to said tube a second chamber in communication with said first chamber through said separating body, and closure means on the end opposite said separating body to confine the passed fraction with said second chamber between said closure means and said separating body, said separating body, when attached to said tube and when subjected, to said centrifugal separating about its vertical axis or a remote or offset axis substantially parallel to the tube's vertical axis, permitting the passing of fluid fractions having particles below said threshold size from said tube through said separating body and into said device, and retaining fluid fractions having particles above said threshold size within said tube, wherein said separate body has a surface confronting said first chamber, said surface extending inwardly and downwardly from the periphery thereof toward the center of said separating body.

2. Device according to claim 1 wherein said end opposite said separating body is in the form of a pipette tip operable to dispense the passed fraction from said device in precisely-defined volumes.

3. The device according to claim 1 wherein the attachment is configured to be coaxial with the blood collection tube.

4. Device according to claim 1 wherein said attachment includes a cap dimensioned to fit over one end of the attachment upon disengagement of said end from said collection tube to thereby constitute said attachment as a transport carrier for said fraction.

5. Apparatus according to claim 1 wherein the opposite end of said second chamber includes a closure cap for closing said second chamber.

6. Apparatus according to claim 1 wherein said second chamber has an outer dimension greater than the outer dimension of said collection tube to generate a differential hydrostatic pressure between said second chamber and said tube.

7. Device according to claim 1 wherein said separating body includes an attachment adapted to releasably engage said open end of said collection tube, said attachment mounting said separating body therein in sealing relation to said collection tube.

8. Device according to claim 7 wherein said separating body is annular and provided with a self-sealing, needle penetratable core centrally therein.

9. Device according to claim 7 wherein said separating body has pores large enough to pass plasma therethrough, but small enough to prevent substantial amounts of blood cells from passing therethrough.

10. Device according to claim 9 wherein the separating body is a substantially solid porous body.

* * * * *

UNITED STATES PATENT AND TRADEMARK OFFICE
CERTIFICATE OF CORRECTION

PATENT NO. : 5,275,731
DATED : January 4, 1994
INVENTOR(S) : Karl H. Jahn

It is certified that error appears in the above-indentified patent and that said Letters Patent is hereby corrected as shown below:

Title page, Abstract, line 1, insert ...a... between the words "having" and "multichamber"

Column 2, line 49, "4,14,690" should read ...4,154,690...
      line 62, the word "in" should be ...is...
Column 12, line 4, the word "a" should be ...at..., and the word "operable" should be ...end...
Column 12, line 13, the word "and" should be ...end...
      line 18, the word "with" should be ...within...
      line 30, the word "separate" should be ...separating...

Signed and Sealed this

Thirteenth Day of September, 1994

Attest:

BRUCE LEHMAN

Attesting Officer                *Commissioner of Patents and Trademarks*

UNITED STATES PATENT AND TRADEMARK OFFICE
CERTIFICATE OF CORRECTION

PATENT NO. : 5,275,731
DATED : January 4, 1994
INVENTOR(S) : Karl H. Jahn

It is certified that error appears in the above-indentified patent and that said Letters Patent is hereby corrected as shown below:

Column 12, line 4, the word "operable" should read--openable--.

Signed and Sealed this

First Day of November, 1994

Attest:

BRUCE LEHMAN

*Attesting Officer*       *Commissioner of Patents and Trademarks*